United States Patent [19]
Reeves

[11] Patent Number: 6,159,977
[45] Date of Patent: Dec. 12, 2000

[54] THERAPEUTIC ANTI-FUNGAL NAIL PREPARATION

[75] Inventor: Stanley Forrest Reeves, Demopolis, Ala.

[73] Assignee: Astan, Inc., Birmingham, Ala.

[21] Appl. No.: 09/193,073

[22] Filed: Nov. 16, 1998

[51] Int. Cl.[7] .......................... A01N 43/58; A01N 43/40; A01N 43/64; A01N 43/50; A01N 47/10

[52] U.S. Cl. .......................... 514/252; 514/273; 514/345; 514/359; 514/396; 514/397; 514/479; 514/570; 514/723

[58] Field of Search ...................... 514/946, 252, 514/359, 570, 345, 723, 396, 397, 272, 479

[56] References Cited

U.S. PATENT DOCUMENTS

| | | | |
|---|---|---|---|
| 4,073,922 | 2/1978 | Wyburn-Mason | 424/273 |
| 4,608,249 | 8/1986 | Otsuka et al. | 424/28 |
| 4,652,557 | 3/1987 | Sandborn | 514/164 |
| 4,721,724 | 1/1988 | Stettendorf et al. | 514/396 |
| 4,927,641 | 5/1990 | Knight | 424/665 |
| 5,151,271 | 9/1992 | Otsuka et al. | 424/443 |
| 5,612,324 | 3/1997 | Guaung Lin et al. | 514/162 |
| 5,683,713 | 11/1997 | Blank et al. | 424/449 |
| 5,874,479 | 2/1999 | Martin | 514/724 |

*Primary Examiner*—Jose' G. Dees
*Assistant Examiner*—Alton Pryor
*Attorney, Agent, or Firm*—Sirote & Permutt, P.C.; Russell Carter Gache; Russell L. Sandidge

[57] ABSTRACT

A therapeutic solution and application procedure for curing Nail fungus infections or Onychomycosis comprising a combination of an anti-fungal agent with DMSO in a anhydrous solution of Polyglycol, and including a secondary anti-inflammatory agent. The DMSO acts as a delivery vehicle so that active anti-fungal agents such as Miconazole in combination with an anti-inflammatory compound such as ibuprofen can be delivered directly to fungal infected areas under and around the nail. The DMSO, Miconazole, and ibuprofen are dissolved in a viscous solution of Polyglycol so that the combined ingredients may be applied directly to the affected nails with superior penetration. The therapeutic solution is formulated by dissolving the Miconazole into the Polyglycol over heat and adding the ibuprofen and DMSO over additional heat in a timed process. Repeated applications of the resulting solution on Onychomycosis infected nails over one 4–6 week period yields satisfactory result rates as high as 85–90% without augmenting the therapy with systemic drugs. Most versions of the therapeutic solution are anticipated to not require a prescription.

18 Claims, No Drawings

THERAPEUTIC ANTI-FUNGAL NAIL PREPARATION

FIELD OF THE INVENTION

The present invention relates generally to therapeutic preparations using dimethyl sulfoxide (DMSO) as a transport mechanism to deliver active agents to infected areas. In particular, the present invention relates to therapeutic preparations using DMSO to deliver anti-fungal agents to infected areas relatively inaccessible to conventional therapeutic compounds.

BACKGROUND OF THE INVENTION

Infections on the exterior of the human body are caused by a variety of micro-organisms, including bacteria, fungi, and molds. Many micro-organisms living on or within the body are beneficial, but others multiply rapidly and may form infections if unchecked by crowding of other micro-organisms or controlling environmental factors. Some organisms such as microscopic plants or fungi can live on the skin and obtain nourishment from dead tissues such as hair, nails, and outer skin layers. When fungi growing on the body grows out of control, an infection can result with detrimental effects to living tissue. In addition, fungal infections are communicable and individuals who frequent public swimming pools, gyms, or shower rooms are susceptible to being infected with various types of fungal infections as other infected individuals visit these public areas.

One type of external micro-organism based infection is Onychomycosis, commonly referred to as "nail fungus." Onychomycosis is an infection of the nail (i.e. unguis) and nail bed cause by pathogenic fungi, among other micro-organisms, and while not life threatening the disease can cause chronic discomfort and embarrassment. The decease attacks the nails and their growth centers making them look cracked, yellow, and highly disfigured. In acute cases, Onychomycosis can cause the nail to become old and yellow, making it easily damaged and from which subungual hemorrhages can result.

Onychomycosis is caused by a variety of micro-organisms such as dermatophytes, yeasts, and molds. However, the majority of Onychomycosis cases are caused by Fungi such as Trichophyton rubrum, Trichophyton mentagrophytes, Trichophyton tonsurans and Epidermophyton floccosum. Once these micro-organisms establish sub-cutaneous growth, eradication with current treatments is difficult and reoccurrences of the stubborn disease is costly.

In recent years Onychomycosis has spread to a higher percentage of adults due, in part, to its contagious nature and the lack of effective medications that can quickly cure the disease once established within the nail bed. Current treatments include long-term (3–9 months) application of topical fungicidal creams in combination with systemic fungal treatment drugs such as grisoefulvin, terbinafine, Lamisil, and Sporonox. Some of the systemic treatments have undesirable side effects such as nausea, headache, photosensitivity, and gastrointestinal intolerance, making the process of eradication difficult and troublesome.

It is also noted that systemic fungal treatments are expensive. A treatment program using Lamisil tablets (250 mg) costs over $600 and a therapy using Sporonox can cost between $600 and $1,200. Conversely, the instant invention contemplates a non-systemic treatment program costing under $50.

Part of the difficulty of quickly curing Onychomycosis is the inability to deliver effective anti-fungal agents to the pathogenically active areas such that all of the pathogenic fungus is eradicated. Without full eradication, reoccurrence is likely, necessitating a new cycle of combined topical and systemic treatments, with the aforementioned systemic side effects. Treatment is complicated by the fact that the cutaneous nail shell is not easily penetrated and treatments of infected areas often require thinning of the nail to allow better penetration of anti-fungal agents. The nail acts as a protective barrier under which fungus can grow unhindered and even acts as a vessel for spreading the disease. Current topical anti-fungal ointments and solutions used to treat Onychomycosis do not penetrate into the nail bed easily and tend to leave some portion of fungus alive after treatment causing reoccurrence of the disease. Heretofore, the medical industry has not produced a topical treatment having the necessary chemical properties to effectively pass through the hard cutaneous nail shell and penetrate into the nail bed for rapid and complete destruction of the fungal infection.

Therefore, there is a need for a topical solution that quickly and thoroughly penetrates the nail shell, underlying nail bed, and surrounding nail tissue to deliver an effective anti-fungal agent that will kill the causes of Onychomycosis.

SUMMARY OF THE INVENTION

It is the object of the present invention to provide a topical solution containing effective anti-fungal agents that will penetrate the hard cutaneous shell of the nail to kill the cause of Onychomycosis disease.

A further object of the present invention is to provide a method of making the penetrating topical solution.

An even further object of the present invention is to provide for a therapeutic treatment procedure for curing Onychomycosis without the advent of systemic drugs.

In summary, the invention provides for a combination of an anti-fungal agent with DMSO in an anhydrous solution of Polyglycol, and including a secondary anti-inflammatory agent. The DMSO acts as a delivery vehicle so that active anti-fungal agents such as Miconazole in combination with an anti-inflammatory such as ibuprofen can be delivered directly to fungal infected areas under and around the nail. The DMSO, Miconazole, and ibuprofen are dissolved in a viscous solution of Polyglycol so that the combined ingredients may be applied directly to the affected nails in a topical solution. The therapeutic solution is created by dissolving the Miconazole into the Polyglycol over heat and adding the ibuprofen and DMSO over heat in a timed process. Repeated applications of the resulting solution on Onychomycosis infected nails over two 4–6 week application periods yields an 85–90% satisfactory result rate without augmenting the topical treatments with systemic drugs. Most versions of the preferred solution may be sold over-the-counter and should cost far less than current methods of Onychomycosis eradication.

Other features and objects and advantages of the present invention will become apparent from a reading of the following description.

DESCRIPTION OF THE PREFERRED EMBODIMENTS

Using DMSO to assist with delivery of chemicals into the blood and tissue is well known. However, use of DMSO to deliver anti-fungal agents and anti-inflammatory agents through and under human nail structure has been heretofore unknown.

In February of 1997, the inventor combined several therapeutic agents with DMSO and conducted experimental trials on human subjects to ascertain the potential for a therapeutic anti-fungal solution and treatment for Onychomycosis. The results were surprising, with satisfactory result rates as high as 85–90% after a twelve (12) week period of treatment, and without systemic drug therapy. In addition, anti-fungal results were seen as early as two weeks after application in many subjects. Such rapid results in Onychomycosis with this delivery system was unknown prior to the study.

After subsequent experimental trials in which various ingredient concentrations were tried and after further variations in compounding techniques were undertaken, a topical therapeutic solution emerged that has the necessary penetrating characteristics to cure Onychomycosis.

DMSO (sometimes referred to chemically as $CH_3(SO)$ is a controversial substance having well known penetrating properties into human tissue. A wide range of primary pharmacological actions of DMSO have been documented in laboratory studies such as: membrane transport, anti-inflammation, analgesia, bactriostasis, non-specific enhancement of resistance to bacteria, vasodilation, muscle relaxation, and reduction in serum cholesterol. While the actual mechanism of penetration enhancement is not precisely known (some studies indicate that increased pedicle flap circulation and histamine liberation are causes), DMSO can act as a carrier of substances into the body for non-ionized molecules of low molecular weight. Studies have also shown that DMSO increases the permeability of the stratum corneum by increasing its water content.

Some studies indicate that solutions of 90% DMSO (by volume) are more effective as a transport carrier than solutions using less than or more than 90%. However, clinical trials using experimental versions of the invention show that using a 40% solution of DMSO provides superior absorption and carrier properties for anti-fungal agents and anti-inflammatories. In particular, the combination of Polyglycol 300 MW (molecular weight), ibuprofen USP (U.S. Pharmacopoeia Standard), and DMSO (99% purity used at 40% by volume) results in an effective carrier for anti-fungal agents such as, for example, Miconazole and Clotrimazole.

Ibuprofen USP $[(Ch_3)_2ChCh_2Ch(Ch_3COOH]$, also known by the trade name Motrin™) is a white crystalline powder with a slight odor which has for some time been known as an anti-inflammatory. When ibuprofen is compounded into a 40% by volume polyglycol solution at 4% by volume amounts, delivery of anti-fungal agents into a sub-cutinal fungus infection is faster than without ibuprofen. The exact reason for this is unknown, but the inventor suspects that either the absorption rate of the anti-fungal agents by the fungus itself is increased or more of the active anti-fungal agents penetrate into the surrounding tissues. Other anti-inflammatory agents besides ibuprofen well known in the art are suspected of also improving the efficacy of the anti-fungal agent.

Polyglycol 300 is a viscous, mostly clear solution which is used as an anhydrous base for the invention. Polyglycol 300 is superior as a solution base because it is non-irritating, it has a low order of toxicity in human tissue, it is soluble in most organic solvents, and is clear and non-staining. Furthermore, Polyglycol 300 has viscous properties which allows better retention of the invention on infected areas, such as a nail, when applied, thereby improving the dosage volume to infected areas.

Although several types of anti-fungal agents may be used in the instant invention, one agent Miconazole USP performs well to kill Onychomycosis. Miconazole USP (1-[2-(2,4-dichloraphenyl)-2-[(2,4-dichloraphenyl)Medthoxy]ethyl]-1h-imidazole mononitrate; also known by the trade name Monistat™) is a white crystalline powder that has been used as primary agent in anti-fungal preparations. The inventor has found that a 4% solution of Miconazole is sufficient to kill the fungi in Onychomycosis when used in a sustained application regime. Other anti-fungal agents effective in fighting the fungi causing Onychomycosis and suitable for use in the present invention are: Clotrimazole, Tioconazole, Nystatin, Terconazole, Butoconazole Nitrate, Unecylenic Acid, Clioquinol, Ciclopirox Olamine, Econazole Nitrate, Triacetin, Tolnaftate, Flucytosine, and Ketoconazole.

A preferred solution embodying the elements of the invention for producing a 100 ml quantity contains 4 grams of ibuprofen USP, 40 ml of DMSO, 4 grams of Miconazole USP, and 100 ml (q.s.) of Polyglycol 300 MW, NF Liquid. To compound the preferred solution, measure out 4 grams of Miconazole and warm 40 ml Polyglycol 300 in a beaker to 45° C. (a temperature range of 40°–50° C. is satisfactory, but 45° C. is optimum). A magnetic stirrer should also be employed to facilitate the mixing of ingredients and a temperature of 45° C. should be maintained in the beaker until all ingredients have been combined. Slowly add the Miconazole by sifting to the Polyglycol and let stir until completely dissolved and uniform into the Polyglycol. Once the Miconazole has completely dissolved, add by sifting 4 grams of ibuprofen USP into the solution and stir until solution is uniform. Measure out 40 ml of DMSO 99% and slowly add to the solution. Remove the heat source and continue stirring for 10–15 minutes until solution is uniform. After uniform, filter the resultant solution through an 80 Mcg filter to remove contaminants and precipitates. The resultant solution will have 4% ibuprofen, 40% DMSO, 4% Miconazole, by volume, in the Polyglycol base. Once the solution reaches room temperature, transfer the solution into storage bottles appropriate for dispensing. Bottles should also be marked with a four year expiration date.

To insure the strength and the stability of the invention solution, the above procedure should be followed. For example, Miconazole is insoluble in water and hence adding it to warmed Polyglycol facilitates the dissolution of Miconazole more quickly. Using a different mixing procedure may prevent proper dissolution of the ingredient thereby weakening the solution. Also, ibuprofen should be added after the Miconazole is dissolved to quicken the dissolving of the ibuprofen, and DMSO, as a strong solvent, should be added to a weaker solvent Polyglycol to, again, facilitate dissolution.

In order to kill pathogenic micro-organisms living in an infected nail, a periodic application regime using the preferred solution is required. Nails infected with Onychomycosis should be cleaned and washed, and allowed to dry. The solution is then applied liberally to the infected area and all parts of the nail. The solution is left to air dry directly onto the infected nail. The application procedure should be repeated 3–4 times daily for 4–6 weeks, depending on THERAPEUTIC ANTI-FUNGAL NAIL PREPARATION the severity of the infection. A 4–6 week application of the invention solution will yield a 85–90% satisfactory result rate in most treatments. Also, the solution can be used against all types of fungi causing Onychomycosis and may be purchased over-the-counter (according to present Food & Drug Administration guidelines).

While I have shown my invention in one form, it will be obvious to those skilled in the art that it is not so limited but is susceptible of various changes and modifications without departing from the spirit thereof. For example, while the invention teaches a combined solution of DMSO with the antifungal agent and ibuprofen, it is contemplated that the antifungal and anti-inflammatory agents may be combined with the Polyglycol into a solution which can be applied directly to an infected nail and to which the DMSO may be added directly thereafter. Other such variations embodying the invention are likewise contemplated.

Having set forth the nature of the present invention, what is claimed is:

1. A topical solution effective in inhibiting the growth of micro-organisms causing Onychomycosis, consisting essentially of:
    a. a pharmacological agent for killing micro-organisms causing Onychomycosis;
    b. an anti-inflammatory;
    c. a polyglycol base into which said agent and said anti-inflammatory are dissolved; and,
    d. a solution of DMSO mixed with said polyglycol base.

2. A topical solution as recited in claim 1, wherein said pharmacological agent is an antifungal agent selected from the group consisting of Miconazole, Clotrimazole, Tioconazole, Nystatin, Terconazole, Butoconazole Nitrate, Unecylenic Acid, Clioquinol, Ciclopirox Olamine, Econazole Nitrate, Triacetin, Tolnaftate, Flucytosine, and Ketoconazole.

3. A topical solution as recited in claim 2, wherein said anti-inflammatory is ibuprofen.

4. A topical solution as recited in claim 3, wherein said ibuprofen is 4% by volume.

5. A topical solution as recited in claim 2, wherein said polyglycol is of the molecular weight of 300.

6. A topical solution as recited in claim 1, wherein said topical solution contains 40% by volume DMSO.

7. A topical solution as recited in claim 1, wherein said pharmacological agent is between 1–30% by volume of said solution.

8. A topical solution as recited in claim 1, wherein said pharmacological agent is Miconazole.

9. A pharmaceutical composition for enhancing penetration of a pharmaceutically active antifungal substance, consisting essentially of:
    a. an antifungal agent selected from the group consisting of Miconazole, Clotrimazole, Tioconazole, Nystatin, Terconazole, Butoconazole Nitrate, Unecylenic Acid, Clioquinol, Ciclopirox Olamine, Econazole Nitrate, Triacetin, Tolnaftate, Flucytosine, and Ketoconazole;
    b. ibuprofen;
    c. a polyglycol base into which said agent and said ibuprofen are dissolved; and,
    d. a solution of DMSO mixed with said polyglycol base.

10. A pharmaceutical composition for enhancing penetration of a therapeutic agent through unguis, consisting essentially of:
    a. an antifungal agent for killing said micro-organisms causing Onychomycosis;
    b. an anti-inflammatory agent for enhancing efficacy of said killing means;
    c. an anhydrous base into which said antifungal agent and said anti-inflammatory agent are dissolved; and,
    d. a solution of DMSO mixed with said anhydrous base for enhancing penetration of said antifungal agent into said unguis.

11. A Pharmaceutical composition as recited in claim 10, wherein said anhydrous base comprises polyglycol.

12. A composition for enhancing transdermal and trans-cutinel penetration of a pharmaceutically active substance, consisting essentially of:
    a. from about 1 to 30% by volume of an antifungal agent;
    b. from about 1 to 40% by volume of ibuprofen;
    c. from about 10 to 80% by volume of a polyglycol base into which said agent and said ibuprofen are dissolved; and,
    d. from about 10 to 80% solution of DMSO mixed with said polyglycol base and in an inverse proportion by volume with said polyglycol base .

13. A method of making a therapeutic solution for inhibiting the growth of micro-organisms causing Onychomycosis, comprising the steps of:
    a. heating and maintaining 40 ml of Polyglycol liquid at 45° C.;
    b. slowly stirring in 4 grams of Miconazole into said heated Polyglycol until dissolved;
    c. adding 4 grams of ibuprofen to said Polyglycol and stirring until uniform;
    d. slowly adding 40 ml of 99% pure DMSO liquid to said Polyglycol; and,
    e. allowing said solution to cool to room temperature while stirring until all ingredients are uniform.

14. The method as recited in claim 13, wherein said Miconazole is sifted into said heated Polyglycol base.

15. The method as recited in claim 13, wherein said ibuprofen is sifted into said heated Polyglycol base.

16. The method as recited in claim 13, wherein said method of making a therapeutic solution includes the additional step of filtering said solution after said cooling step.

17. The method as recited in claim 13, wherein said step of stirring in Miconazole comes after said step of adding ibuprofen.

18. A method of killing micro-organisms causing nail fungus, comprising the step of applying to a nail a solution effective in eliminating fungi, said solution consisting essentially of:
    a. an anti-fungal agent selected from the group consisting of Miconazole, Clotrimazole, Tioconazole, Nystatin, Terconazole, Butoconazole Nitrate, Unecylenic Acid, Clioquinol, Ciclopirox Olamine, Econazole Nitrate, Triacetin, Tolnaftate, Flucytosine, and Ketoconazole;
    b. ibuprofen;
    c. a polyglycol base into which said agent and said ibuprofen are dissolved; and,
    d. a solution of DMSO mixed with said polyglycol base.

* * * * *

UNITED STATES PATENT AND TRADEMARK OFFICE
CERTIFICATE OF CORRECTION

PATENT NO. : 6,159,977
DATED : December 12, 2000
INVENTOR(S) : Stanley Forrest Reeves It is certified that error appears in the above-identified patent and that said Letters Patent are hereby corrected as shown below:

under DESCRIPTION OF THE PREFERRED EMBODIMENTS, column 4, line 58, delete "THERAPEUTIC ANTI-FUNGAL NAIL PREPARATION".

Signed and Sealed this

Eighth Day of May, 2001

*Attest:*

NICHOLAS P. GODICI

*Attesting Officer*   *Acting Director of the United States Patent and Trademark Office*